United States Patent [19]
Roth

[11] Patent Number: 5,315,512
[45] Date of Patent: May 24, 1994

[54] APPARATUS AND METHOD FOR GENERATING IMAGE REPRESENTATIONS OF A BODY UTILIZING AN ULTRASONIC IMAGING SUBSYSTEM AND A THREE-DIMENSIONAL DIGITIZER SUBSYSTEM

[75] Inventor: James A. Roth, Dobbs Ferry, N.Y.

[73] Assignee: Montefiore Medical Center, Bronx, N.Y.

[21] Appl. No.: 402,904

[22] Filed: Sep. 1, 1989

[51] Int. Cl.⁵ .............................................. G06F 15/42
[52] U.S. Cl. ............................ 364/413.25; 128/660.07
[58] Field of Search .............. 128/660.07; 364/413.25; 73/660; 358/440, 441

[56] References Cited

U.S. PATENT DOCUMENTS

| | | | |
|---|---|---|---|
| Re. 30,397 | 9/1980 | King | 128/660 |
| 4,130,022 | 12/1978 | Goodrich et al. | 73/633 |
| 4,390,025 | 6/1983 | Takemura et al. | 128/660.04 |
| 4,431,007 | 2/1984 | Amazeen et al. | 73/626 |
| 4,444,197 | 4/1984 | Koyano et al. | 128/660.07 |
| 4,703,439 | 10/1987 | Lotz | 364/521 |
| 4,747,411 | 5/1988 | Ledley | 128/660 |
| 4,855,910 | 8/1989 | Bohning | 364/413.13 |
| 4,879,668 | 11/1989 | Cline et al. | 364/522 |
| 4,932,414 | 6/1990 | Coleman et al. | 128/660.09 |

FOREIGN PATENT DOCUMENTS

0452532A1 10/1991 European Pat. Off. .
WO9013259 11/1990 PCT Int'l Appl. .

OTHER PUBLICATIONS

Roth et al., "Voxel-Based Three-Dimensional Cardiac Echo Reconstruction: In Vitro Validation", Poster, Clinical Research, vol. 36, Apr., 1988.

Moritz et al., "An Ultrasonic Technique For Imaging The Ventric In Three Dimensions And Calculating Its Volume", IEEE Transactions On Biomedical Engineering, vol. BME-30, No. 8, 1983.

Brinkley et al., "Fetal Weight Estimation From Lengths And Volumes Found By Three-Dimensional Ultrasonic Measurements", Journal Of Ultrasound In Medicine, vol. 3, Apr. 1984.

Blankenhorn et al., "Work In Progress: Common Carotid Artery Contours Reconstructed In Three Dimensions From Parallel Ultrasonic Images", Radiology vol. 148 No. 2, Aug. 1983.

(List continued on next page.)

*Primary Examiner*—Gail O. Hayes
*Attorney, Agent, or Firm*—Martin Novack

[57] ABSTRACT

The disclosure is directed to an apparatus and method for producing a three-dimensional image representation of a body. The body can be animate or inanimate; i.e. the invention can be used to obtain 3D image representations of for example, parts of the human body or any object that one wishes to view or measure. The 3D image representations can be used to produce 2D displays of sections, contours, etc., or displays having 3D perspective, such as wire-frame type illustrations. This facilitates automatic computation of areas or volumes. In a disclosed embodiment, an ultrasonic imaging subsystem is provided for producing signals representative of two-dimensional images of sections of the body, the subsystem including a scanning transducer that is moveable to determine the section of the body to be imaged. The image representative signals are stored as arrays of digital pixel values. A three-dimensional acoustic digitizer subsystem is provided for deriving and storing information representative of the position and orientation of the transducer during the scanning of an associated section of the body. A voxel space storage is provided for storing a three-dimensional array of voxel values. The arrays of digital pixel values are projected into the voxel space storage, the voxel locations which correspond to projected pixel locations of a given pixel array being determined as a function of the stored position and orientation information associated with the section of the body from which the given pixel array was obtained.

16 Claims, 14 Drawing Sheets

OTHER PUBLICATIONS

Brinkley et al., "Ultrasonic Three-Dimensional Imaging And Volume From A Series Of Arbitrary Sector Scans", Ultrasound In Medicine & Biology, vol. 4, 1978.

Talano et al., "Textbook of Two-Dimensional Echocardiography", chapter 16, Grune & Stratton, Inc., 1983.

Geiser et al., "A Framework For Three-Dimensional Time-Varying Reconstruction Of The Human Left Ventricle: Sources Of Error and Estimation Of Their Magnitude", Computers And Biomedical Research 13, 225–241, 1980.

Geiser et al., "Dynamic Three-Dimensional Echocardiographic Reconstruction Of The Intact Human Left Ventricle: Technique And Initial Observation In Patients", Progress In Cardiology, 1982.

E. A. Geiser, "Three-Dimensional Echocardiographic Reconstruction: How Does It Stack Up?", International Journal of Cardiology 7, 77–81, 1985.

Skorton et al., "New Directions In Echo-Cardiography", Cardio, Mar., 1986.

Wyatt et al., "Cross-Sectional Echocardiography III. Analysis Of Mathematic Models For Quantifying Volume Of Symmetric And Asymmetric Left Ventricles", American Heart Journal, vol. 100, No. 6, Dec., 1980.

Runge et al., "Respiratory Gating In Magnetic Resonance Imaging at 0.5 Tesla", Radiology, 1984.

Dekker et al., "A System For Ultrasonically Imaging The Human Heart In Three Dimensions", Computers And Biomedical Research 7, 544–553, 1974.

APPARATUS AND METHOD FOR GENERATING IMAGE REPRESENTATIONS OF A BODY UTILIZING AN ULTRASONIC IMAGING SUBSYSTEM AND A THREE-DIMENSIONAL DIGITIZER SUBSYSTEM

BACKGROUND OF THE INVENTION

This invention relates to imaging of bodies and, more particularly, to an apparatus and method for generating image representations of a body. The invention has application to both animate and inanimate bodies.

There are many applications where it is useful to obtain an accurate three-dimensional image representation of a body. For example, in manufacturing or testing of objects having irregular shapes, it may be necessary or desirable to have information concerning one or more properties of the object: its surface shape, coordinates and area; the nature and shape of any of its cross-sections; and the volume it contains. Equipment for obtaining these properties tends to be complex and expensive, and often provides information that is incomplete and/or requires operator approximations and calculations.

In clinical applications, the task is further complicated by the inaccessibility, mechanical instability, and fragility of the organs to be imaged or measured. The human heart provides a difficult challenge in this regard.

Understanding the complex time-varying three-dimensional geometry and function of the heart has been the fundamental goal of cardiac imaging. Desirable techniques should be simple to use, safe, and inexpensive to meet the potentially vast clinical demand. Although magnetic resonance imaging and ultra-fast X-Ray computed tomography have the potential to provide precise 3D cardiac imaging, both are expensive and have limited availability. By contrast, monographic techniques including 2D real-time echocardiography are readily available, inexpensive, and pose no known risk to the patient. Despite these potential advantages, practical 3D echocardiography has been an elusive goal. This has been a consequence of both the rigorous demands of cardiac imaging and the difficulty of automating the image generation process, an essential requirement in a clinical setting. Prior investigators have reported techniques which permit a hand-held 2D sector transducer to be tracked in three dimensions. By recording these spatial data along with the 2D images and electrocardiogram, it has been possible to extract selected 2D planes, delineate their endocardial or epicardial contours, and derive an interpolated wire-frame surface in three-dimensions. However, because of the present inability to reliably perform endocardial edge detection by automated techniques, the requirement for antecedent edge detection of multiple selected 2D sections requires that an operator select a small subset of sectors in which hand-guided edge detection is carried out. The resultant 3D reconstruction reflects only the selected contours and is devoid of the rich anatomic detail intrinsic to the primary ultrasound backscatter data.

It is among the objects of the present invention to provide an apparatus and method for obtaining three dimensional image representations that overcome the difficulties and limitations of prior art techniques.

SUMMARY OF THE INVENTION

The present invention is directed to an apparatus and method for producing a three-dimensional image representation of a body. The body can be animate or inanimate; i.e. the invention can be used to obtain 3D image representations of, for example, parts of the human body or any object that one wishes to view or measure. The 3D image representations can be used to produce 2D displays of sections, contours, etc., or displays having 3D perspective, such as wire-frame type illustrations. This facilitates automatic computation of areas or volumes.

In accordance with an embodiment of the apparatus of the invention, an ultrasonic imaging subsystem is provided for producing signals representative of two-dimensional images of sections of the body, the subsystem including a scanning transducer that is moveable to determine the section of the body to be imaged. Means are provided for storing the image representative signals as arrays of digital pixel values. Means, including a three-dimensional acoustic digitizer subsystem, are provided for deriving and storing information representative of the position and orientation of the transducer during the scanning of an associated section of the body. A voxel space storage means is provided for storing a three-dimensional array of voxel values. Means are provided for projecting the arrays of digital pixel values into the voxel space storage means, the voxel locations which correspond to projected pixel locations of a given pixel array being determined as a function of the stored position and orientation information associated with the section of the body from which the given pixel array was obtained.

In a preferred embodiment of the invention, each of the digital pixel values represents one of a multiplicity of gray scale values. Also in this embodiment, the means for projecting the arrays of digital pixel values into the voxel space storage means includes means for determining the voxel locations for a particular pixel array by computing a given voxel location as a function of the two-dimensional coordinates of a given pixel being projected and of the position and orientation information, and then by computing subsequent voxel locations for subsequently projected pixels by taking values obtained during computation of the projected location of a neighboring pixel and adding a value which depends on the incrementing of the pixel coordinates with respect to the neighboring pixel. Also in this embodiment, the means for projecting the arrays of digital pixel values into the voxel space storage means includes means for determining if an existing non-zero gray scale value is already present (indicating an occupied voxel) at a given voxel location to which a current pixel value is projected and, if so, for averaging the current pixel value with the existing voxel value and storing the resulting average value as a new voxel value at the given voxel location.

In a form of the invention, a second voxel space storage means is provided for storing a three dimensional array of voxel values, the second voxel space storage means having a small fraction of the number of voxels of the first-mentioned voxel storage space means. In this form of the invention, the projecting means includes means for projecting lower resolution versions of the pixel arrays into the second voxel space storage means in real-time with respect to the obtainment of said signals representative of two-dimensional images of sections of the body.

Further features and advantages of the invention will become more readily apparent from the following detailed description when taken in conjunction with the accompanying drawings.

BRIEF DESCRIPTION OF THE DRAWINGS

FIG. 5, which includes

FIG. 8, which includes

FIG. 10, which includes

DESCRIPTION OF THE PREFERRED EMBODIMENT

Figure 1:
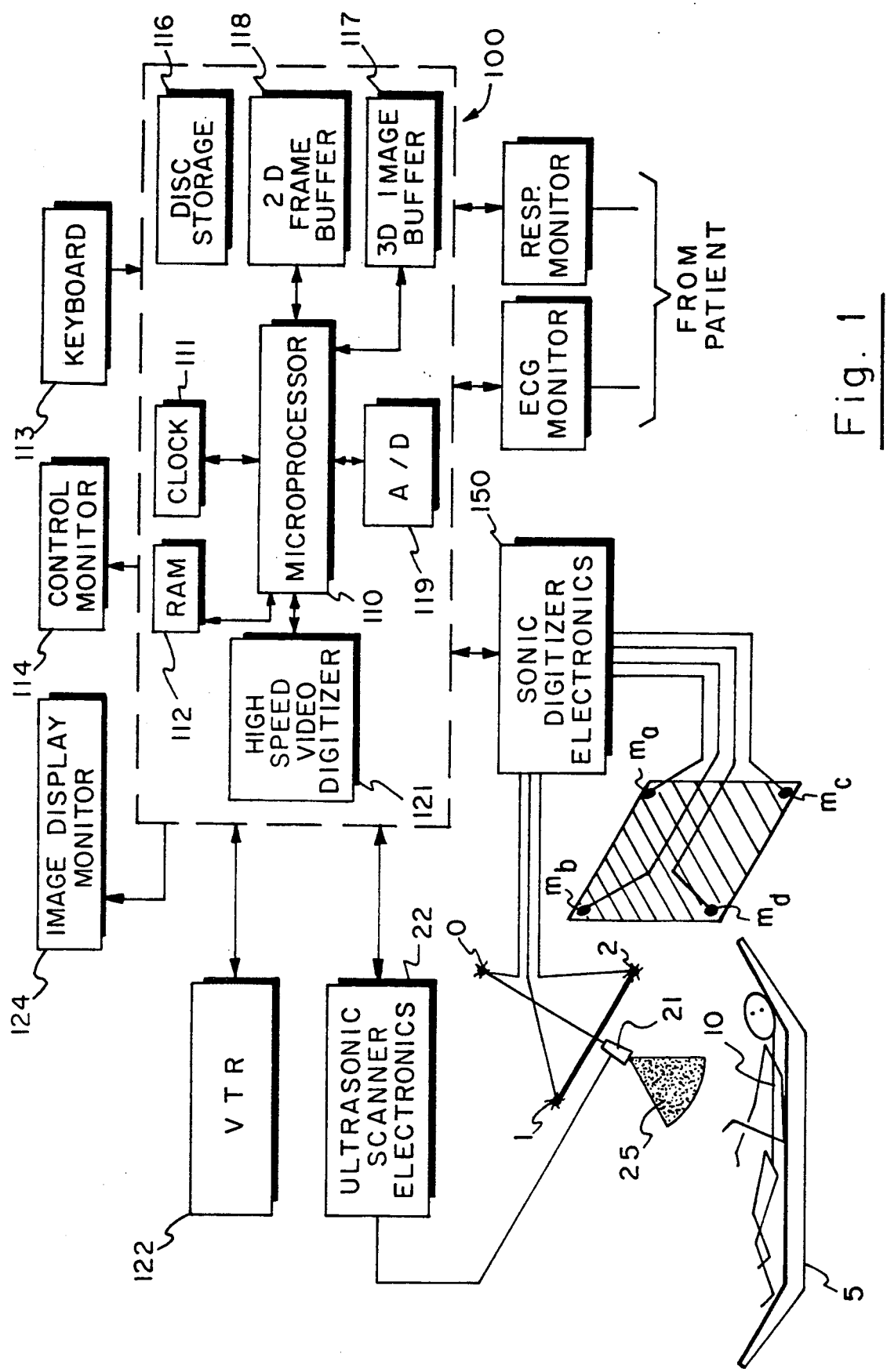
FIG. 1 is a schematic diagram, partially in block form, of an apparatus in accordance with an embodiment of the invention and which can be used to practice an embodiment of the method of the invention.

Referring to FIG. 1, there is shown a block diagram of an apparatus in accordance with an embodiment of the invention and which can be used to practice an embodiment of the method of the invention. A patient 10 or object to be imaged is positioned on an examination table 5 or any suitable location. [The invention can be utilized for examination of both animate and inanimate bodies, but is primarily described herein in terms of examination of a human body, and especially the human heart for which it has particularly advantageous application.] The table 5 can be equipped with means (not shown) for consistently positioning patients so that the chest cavity is in an.approximately predetermined position and orientation, and is maintained as such. While this facilitates operation, it will be understood that the body to be imaged need not be in a particular predetermined position or orientation. In an operating example of the invention, studies were performed with the patient resting supine or in a partial left-sided recumbent position. To minimize patient motion during study, position was stabilized by resting the patient on a radiographic bead cushion which molds to the patient contour when air is evacuated. Because of the inconsistency of cardiac position achieved with voluntarily arrested respiration, patients were encouraged to breathe normally during study.

A two-dimensional ultrasonic imaging subsystem is provided, and includes a transducer 21 that is coupled to processing electronics 22. Ultrasonic imaging systems which provide a two-dimensional image of a "slice" of a body are well known in the art and various types are commercially available. Any suitable type of two-dimensional imager can be employed. An operating embodiment of the invention utilized a Hewlett-Packard Model 77020AC real-time ultrasonic sector scanner having a transducer that includes a 3.5 MHz linear phased array of transducer elements. The transducer produces a beam of ultrasound that is scanned along one direction, i.e. transverse the direction in which the transducer is pointed. The other direction of the two-dimensional scanner is depth into the body. As is well known, an imaging system of this type can produce an image of a cross-section in a body, a sector at a time; i.e., each imaged region is in the general shape of a sector of a circle (as illustrated in FIG. 1 at 25). It will be understood that other types of ultrasonic imaging equipment could be employed, for example an imaging system utilizing mechanical scanning of one or more transducer elements.

The output of imaging subsystem 21, 22 is coupled to a processor subsystem 100. The processor subsystem includes a suitable microprocessor CPU 110, which is conventionally provided with clock circuitry 111, general purpose RAM memory 112, and input/output capability, typically including a keyboard 113 and control monitor 114. In the present embodiment, the processor subsystem 100 is also provided with magnetic disk memory 116, a random access 3D frame buffer 117, random access 2D frame buffer 118, and analog-to-digital converter circuitry 119. A high speed video digitizer 121 is also provided for digitizing video inputs such as from the imaging subsystem 21, 22 or from a video tape recorder 122. An image display monitor 124 is provided for displaying 2D images and two-dimensional representations of 3D images. The processor subsystem may also be provided with a 2D/3D graphics package, which may be of a commercially available type, for displaying 2D or 3D images from stored pixels or voxels in the 2D and 3D frame buffers, respectively. In an operating embodiment of the invention, the microprocessor utilized was an Intel 80286 in an IBM AT Model 339, and the video digitizer was a TARGA M8, AT&T Electronic Photography And Imaging Center, Indianapolis, Ind. As will be described further hereinbelow, the present embodiment utilizes electrocardiogram (ECG) and respiratory readings on the patient for gating of the imaging data. These inputs are represented in FIG. 1 as being generated by monitors 131 and 132, respectively. In an operating embodiment of the invention, an electrocardiographic trigger (131) was used to generate a microprocessor interrupt thereby permitting identification of the onset of each cardiac cycle. A transthoracic impedance plethysmograph (132) was used to generate a low frequency analog respiratory waveform which was digitized by A/D converter 119.

Figure 2:
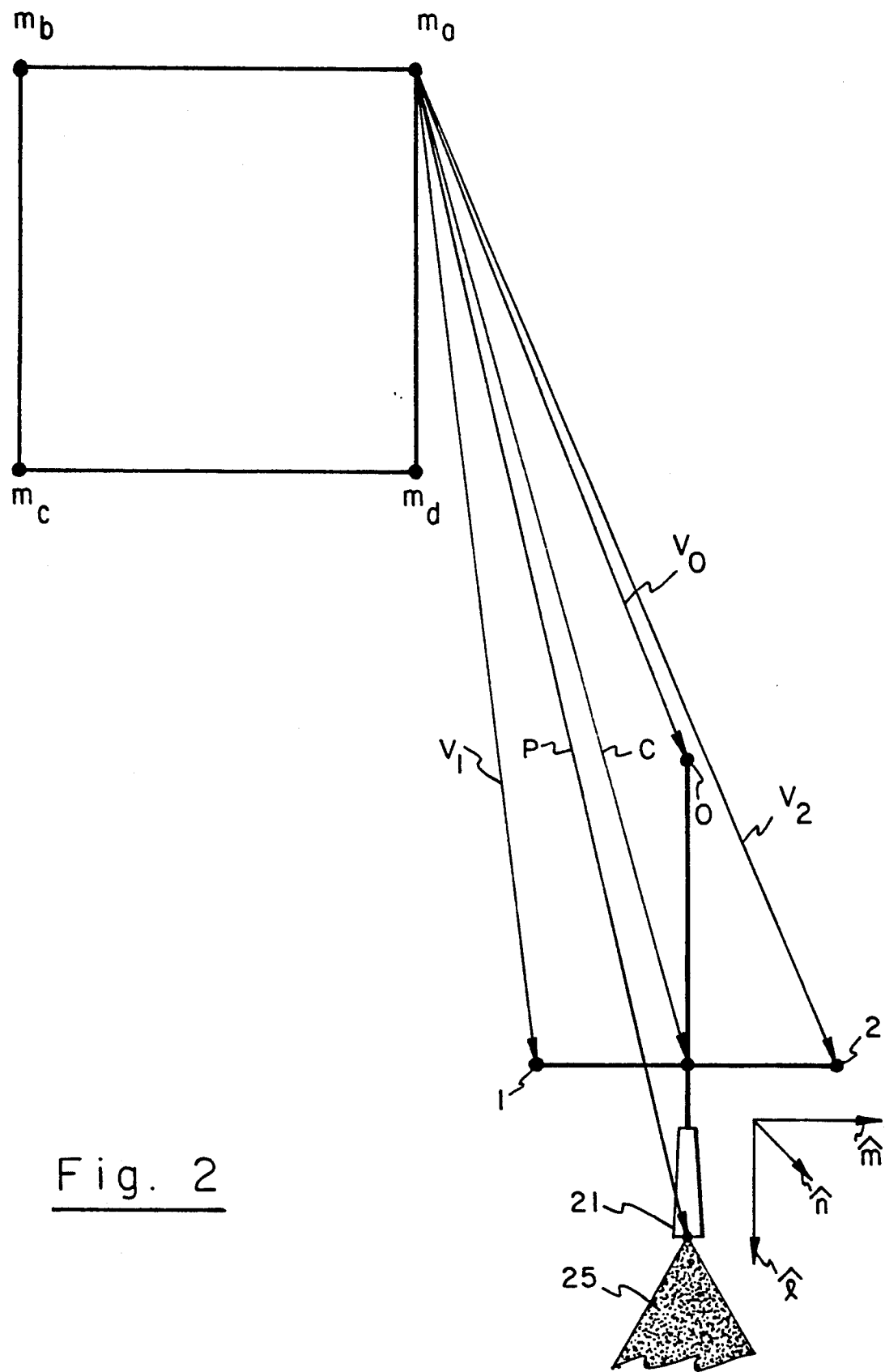
FIG. 2 illustrates the position and orientation of the transducer, and the unit vectors utilized to define the transducer orientation.

In the present embodiment, the three dimensional position and orientation of the 2D phased array transducer is monitored by acoustic ranging utilizing a 3D sonic digitizer 150 which, in an operating embodiment, was a Model GP-8-3D, sold by Science Accessories Corp. of Stratford, Conn. The 3D sonic digitizer is capable of real-time tracking of the location of up to 8 points in three-dimensional space. Point coordinates can be ascertained to within approximately 1 mm. within a region of interest 6×6×6 feet. Four rectangularly mounted microphones, designated $M_a$, $M_b$, $M_c$ and $M_d$ in FIG. 1, are affixed to a suitable reference plane, for example a rigid panel hinged to the wall above the examination table. The orientation of the panel can be angulated upwards approximately 30 degrees from horizontal to maximize exposure with the patient partially rotated to the left during study. Surrounding reflective surface can be covered with acoustically absorbent material to prevent spurious sound reflections. The location and orientation of the transducer 21 is tracked by an array of three spark gap sound emitters designated 0, 1 and 2 mounted in an inverted cross configuration on the shaft of the transducer. This configuration is advantageous in that it results in a large sound emitter separation and, because of its low profile. rarely obstructs the direct propagation of sound to the microphones. These factors decrease both the absolute errors in sound emitter localization as well as the errors propagated to the ultimate localization of pixels in the scan plane. A fourth sound emitter (not shown) can be mounted a known distance from one of the microphones and used to calibrate the 3D digitizer based on the sound propagation velocity during each study. For data acquisition the four sound emitters of the GP-8-3D are triggered in sequence and the interval between sound emission and reception by each of the microphones registered by the sonic digitizer. This results in the four slant ranges ($S_a$, $S_b$, $S_c$ and $S_d$) for each of the three mobile sound emitters, 0, 1 and 2. Orthogonal coordinates (x,y,z) are calculated for each sound emitter as follows:

$$x = (S_a^2 - S_b^2 + S_c^2 - S_d^2 + 2 L_{ab}^2)/(4 L_{ab}) \quad (1)$$

$$y = (S_a^2 + S_b^2 - S_c^2 - S_d^2 + 2 L_{ac}^2)/(4 L_{ac}) \quad (2)$$

$$z^2 = (S_a^2 + S_b^2 + S_c^2 + S_d^2)/4 - (x^2 + (L_{ab}-x)^2 + y^2 + (L_{ac}-y)^2)/2 \quad (3)$$

where $L_{ab}$ is the distance between $M_a$ and $M_b$, and $L_{ac}$ is the distance between $M_a$ and $M_c$. When this computation is made for each sound emitter, three vectors $V_0$, $V_1$, and $V_2$ are derived, as shown in FIG. 2, from an origin at one of the microphones to the sound emitters 0, 1 and 2, respectively. These vectors completely define the position and orientation of the transducer 21. For subsequent computation and processing, it is convenient to derive a set of three orthogonal unit vectors which define the scan plane orientation; a unit vector $\hat{l}$ oriented down the scan plane vertical axis, a unit vector $\hat{m}$ along the plane horizontal axis, and a unit vector $\hat{n}$ normal to the plane, as seen in FIG. 2. The cross point of the cross bar is designated C, so $$C = (V_1 + V_2)/2 \quad (4)$$

The unit vectors can then be derived as:

$$\hat{l} = \frac{(C - V_0)}{|C - V_0|} \quad (5)$$

$$\hat{m} = \frac{(V_2 - V_1)}{|V_2 - V_1|} \quad (6)$$

$$\hat{n} = \hat{l} \times \hat{m} \quad (7)$$

A fourth vector P is developed, and is taken to the apex of the 2D sector, as seen in FIG. 2, to describe the plane's absolute position, as follows:

$$P = C + a\hat{l} \quad (8)$$

Where a is a scaler determined by the distance between the cross point of the cross bar and the transducer surface. In the present embodiment, the transducer orientation [as defined by $\hat{l}$, $\hat{m}$, and $\hat{n}$] and the transducer position [as defined by P] are determined at 120 ms. intervals, yielding eight sets of spatial data per second.

In operation of the present embodiment, an operator can acquire 2-D real-time scans by using the spatially tracked, hand-held transducer and progressing, for example, from cardiac base to apex. In each intercostal space the transducer can be angulated to scan an approximate wedge. Although transducer orientation is adjusted freely to avoid rib and lung, an approximate parasternal short axis orientation has been found to be most effective in delineating the extent of the left ventricular endocardium, left atrium and mitral apparatus. During periods when transducer skin coupling is lost or interposed structures prevent satisfactory 2D imaging, acquisition can be interrupted by release of an operator controlled hand switch (not shown).

When static structures are imaged, timing is not critical. Image data can then be digitized immediately and, for example, stored to magnetic disk during acquisition. However, during dynamic cardiac studies, processing is simplified by deferring image digitization. As will be described, the more desirable images can then be selected retrospectively. In the present embodiment, running time is kept track of by incrementing a 32 bit counter at 10 msec intervals by a dedicated background task invoked by the microcomputer time-of-day clock and encoded in machine readable format with the image data on videotape. By referencing all digitally acquired data to the same counter, subsequent correlation with the video taped image data is straightforward. For implementations where the microprocessor subsystem has limited computational capacity, it may not be possible to carry out a full resolution voxel based reconstruction simultaneously with study acquisition. To facilitate systematic acquisition in such case, the present embodiment provides a reduced resolution 3D reconstruction to guide the operator, as described further hereinbelow.

Simultaneously with 2D image acquisition, the sonic digitizer is interrogated and spatial data processed to compute the echocardiographic transducer orientation and position. In the present embodiment, to facilitate relation of imaging to a patient-referenced coordinate system, the patient coordinate system is defined by three points on the chest (FIG. 3) that are designated and digitized by the operator at the outset of the study: the approximate expected location of the medial extent of the cardiac base (point b), the approximate location of the cardiac apex (point a) and a anterior chest point (point e) taken lateral to b. The vectors to the points a, b and e (from the same origin as the previous vectors) are designated A, B, and E, respectively. The reconstruction space patient-referenced axes can then be defined by unit vectors along the base-apex axis ($\hat{k}$), along an orthogonal anterior-posterior axis ($\hat{i}$) and along a mutually orthogonal medial-lateral transverse axis ($\hat{j}$).

Figure 3:
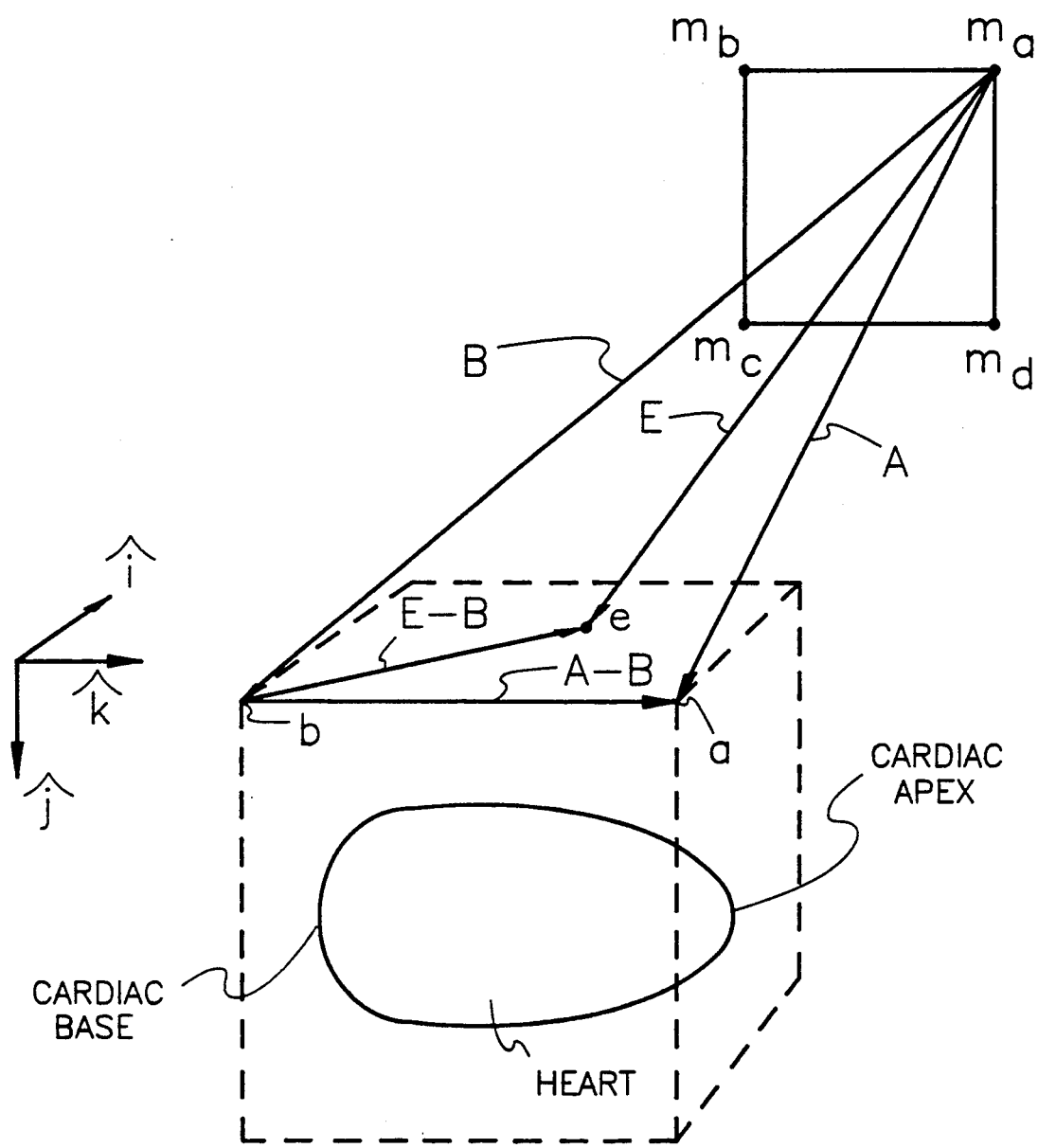
FIG. 3 illustrates the patient-referenced coordinate system utilized in an embodiment of the invention.

These are shown in FIG. 3, and can be derived from A, B and E as follows:

$$\hat{k} = \frac{(A - B)}{|A - B|} \quad (9)$$

$$\hat{j} = \hat{k} \times \frac{(E - B)}{|E - B|} \quad (10)$$

$$\hat{j} = \hat{k} \times \hat{i} \quad (11)$$

The manner in which these are used for reconstruction will be treated momentarily.

Figure 5A:
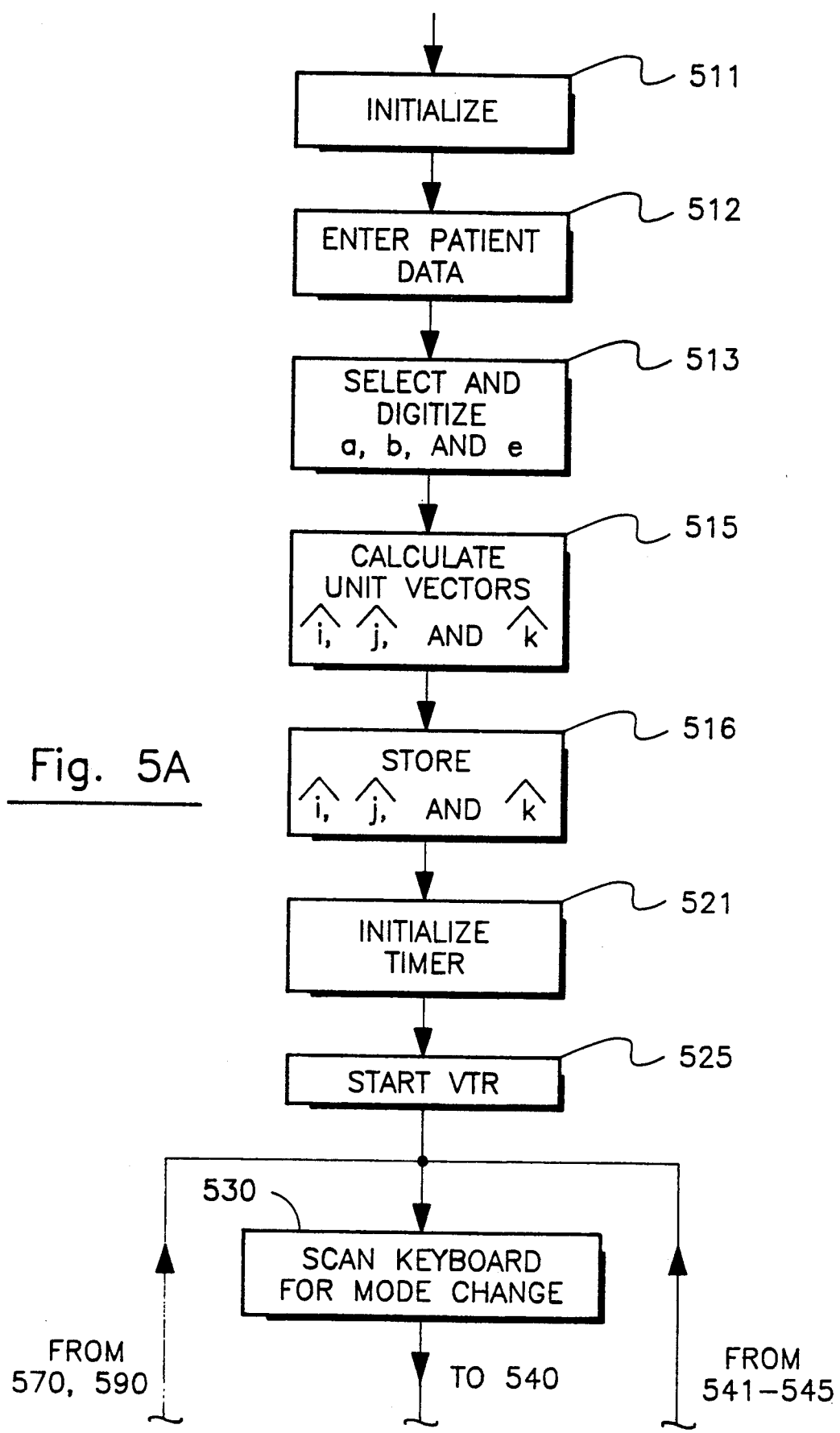
FIGS. 5A and 5B, is a flow diagram of a routine for programming the processor for acquiring data in accordance with an embodiment of the invention.
Figure 5B:
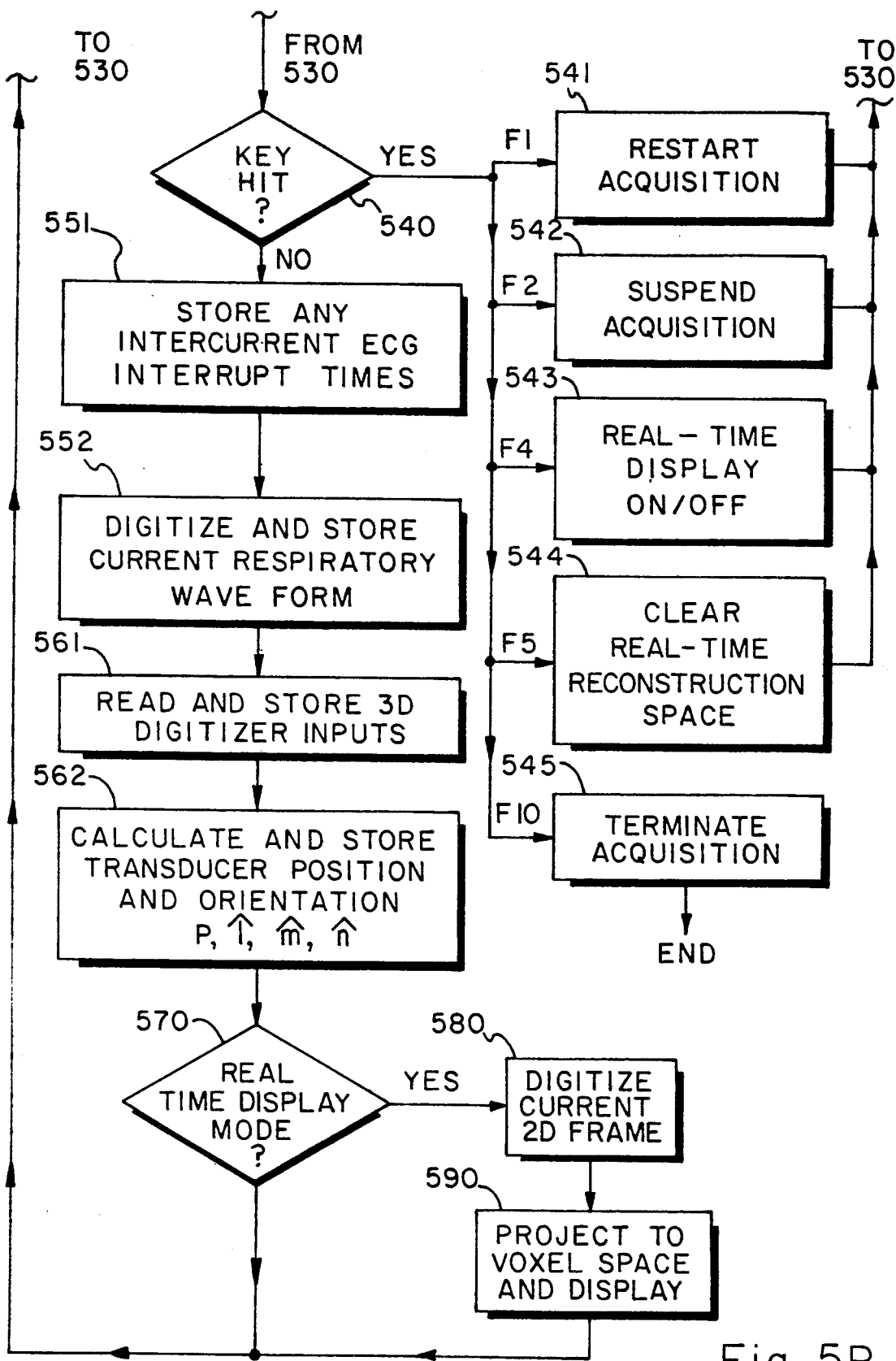

In an operating embodiment hereof, respiratory phase and electrocardiogram were monitored using three conventional Ag-AgCl skin patch chest electrodes positioned to maximize the impedance plethysmographic respiratory waveform while maintaining an adequate ECG waveform for triggering. The timing of electrocardiographic trigger events was stored digitally and used subsequently to define the onset of ventricular systole. The respiratory waveform was digitized at 8 samples/second and stored digitally. The configuration used during acquisition is shown in FIG. 5.

After acquisition of the 2D imaging data, cardiac cycle length can be utilized to reject cycles falling outside a range specified by the operator. Cycles which fail this criterion are excluded together with the ensuing cycle to exclude post-extrasystolic cycles from reconstruction. To correct for cardiac respiratory motion, cycles not falling at the end of expiration are excluded by operator-selected criteria.

A sequence of phases of the cardiac cycle is selected before and after the ECG trigger pulse. Because ECG gating is performed retrospectively, selection of frames preceding the onset of ventricular contraction is feasible permitting accurate superposition of late diastolic events following atrial systole. In the present embodiment, a table of target times generated from the ECG timing data is correlated with the available spatial and respiratory data. Cycles for which there is no valid spatial data within 100 msec of the specified target time, or which fall outside the previously specified end-expiratory window, can be excluded from further analysis. It will be understood that various types of ECG and respiratory gating are known in the art, and other suitable techniques can be used in conjunction with the present invention.

The voxel-based reconstruction constitutes a mapping from the pixel space of the spatially localized 2D sectors to a three-dimensional voxel space. In an operating embodiment of the invention, the gridwork of voxels is stored in a voxel memory space consisting of $128 \times 128 \times 128$ voxels (memory 117 of FIG. 1). In the completed reconstruction, each voxel is represented by 8 bits allowing one of 256 gray levels to be assigned to each. Transformation from the pixel to voxel space requires specification of additional parameters; namely,, the horizontal and vertical 2D image scale, $s_h$ and $s_v$, in millimeters per pixel, and a reconstruction scale $s_{vox}$ for the 3D voxel space in millimeters per voxel. It will be recalled that B is the vector defining the origin of the i, j, k coordinate space, and it can be modified to translate the anatomic region of interest in the voxel reconstruction space. The image scale factors $s_h$ and $s_v$ may be measured from the digitized echo scanner screen, such as by scanning a standard ultrasound calibration phantom (American Institute of Ultrasound in Medicine) or by accepting the internal scanner calibration. Both $s_{vox}$ and B can be chosen at the operator's discretion to appropriately scale and center the reconstruction in the voxel space. In terms of the plane position vectors ($\hat{l}$, $\hat{m}$, and P) and the 2D plane pixel horizontal (h) and vertical (v) coordinates of a pixel, the three dimensional voxel coordinates $i_{vox}$, $j_{vox}$, and $k_{vox}$, in the $\hat{i}$, $\hat{j}$ and $\hat{k}$ directions, respectively, can be expressed as:

$$i_{vox} = [(s_h h)\hat{m} + (s_v v)\hat{l} + P - B] \cdot \hat{i} \quad (12)$$

$$j_{vox} = [(s_h h)\hat{m} + (s_v v)\hat{l} + P - B] \cdot \hat{j} \quad (13)$$

$$k_{vox} = [(s_h h)\hat{m} + (s_v v)\hat{l} + P - B] \cdot \hat{k} \quad (14)$$

In the equations (12), (13) and (14), and subsequently, $s_{vox}$ is assumed to be unity for simplification. In actuality each expression on the righthand side of these equations would be divided by $s_{vox}$.

To decrease the computational burden of obtaining the voxel space coordinates corresponding to each pixel of the 2D image plane, equations (12), (13) and (14) can be rearranged to a form that permits deriving of coordinates for neighboring pixels with the use of simple additions. Equations (12), (13) and (14) can be rearranged as equations (12a), (13a) and (14a), respectively, as follows:

$$i_{vox} = h(s_h \hat{m} \cdot \hat{i}) + v(s_v \hat{l} \cdot \hat{i}) + (P \cdot \hat{i} - B \cdot \hat{i}) \quad (12a)$$

$$j_{vox} = h(s_h \hat{m} \cdot \hat{j}) + v(s_v \hat{l} \cdot \hat{j}) + (P \cdot \hat{j} - B \cdot \hat{j}) \quad (13a)$$

$$k_{vox} = h(s_h \hat{m} \cdot \hat{k}) + v(s_v \hat{l} \cdot \hat{k}) + (P \cdot \hat{k} - B \cdot \hat{k}) \quad (14a)$$

In each of these equations, the quantities in the parentheses are all constants for a particular 2D image plane (with B being a constant for all 2D image planes in a particular study). Thus, for a given image plane, the terms in parenthesis need be computed only once, and then h and v for each pixel position can be suitable incremented to derive the corresponding voxel position coordinates. The pixel value of the projected pixel is stored at the voxel location to which the pixel is projected. This is done for each pixel of each 2D image plane to be projected.

If sufficient computing speed and memory are available, the described functions hereof can be performed in real-time at full resolution. However, in a presently more economical system, where full resolution reconstruction into voxel space is performed after prior obtainment and storage of at least some of the 2D image planes, an embodiment of the invention provides a reduced resolution voxel reconstruction and display in real-time. This is achieved by mapping less pixels (e.g. ¼ as many as the full 2D image resolution) into a second voxel space storage having a small fraction (i.e., less than half) of the number of voxels as the full resolution voxel space storage. In the present embodiment, the second voxel space storage is $32 \times 32 \times 32$ and uses 1/64 [i.e. $(\frac{1}{4})^3$] as many voxels as the full resolution voxel space storage. It will be understood that part of the 3D frame buffer 117 can be used as the second voxel space storage during image acquisition, if such storage is not otherwise being used e.g. to currently compile a full resolution voxel reconstruction. Any available RAM memory in the system can be used for the second voxel space storage (or, for that matter, for the primary voxel space storage if of sufficient size).

Figure 4:
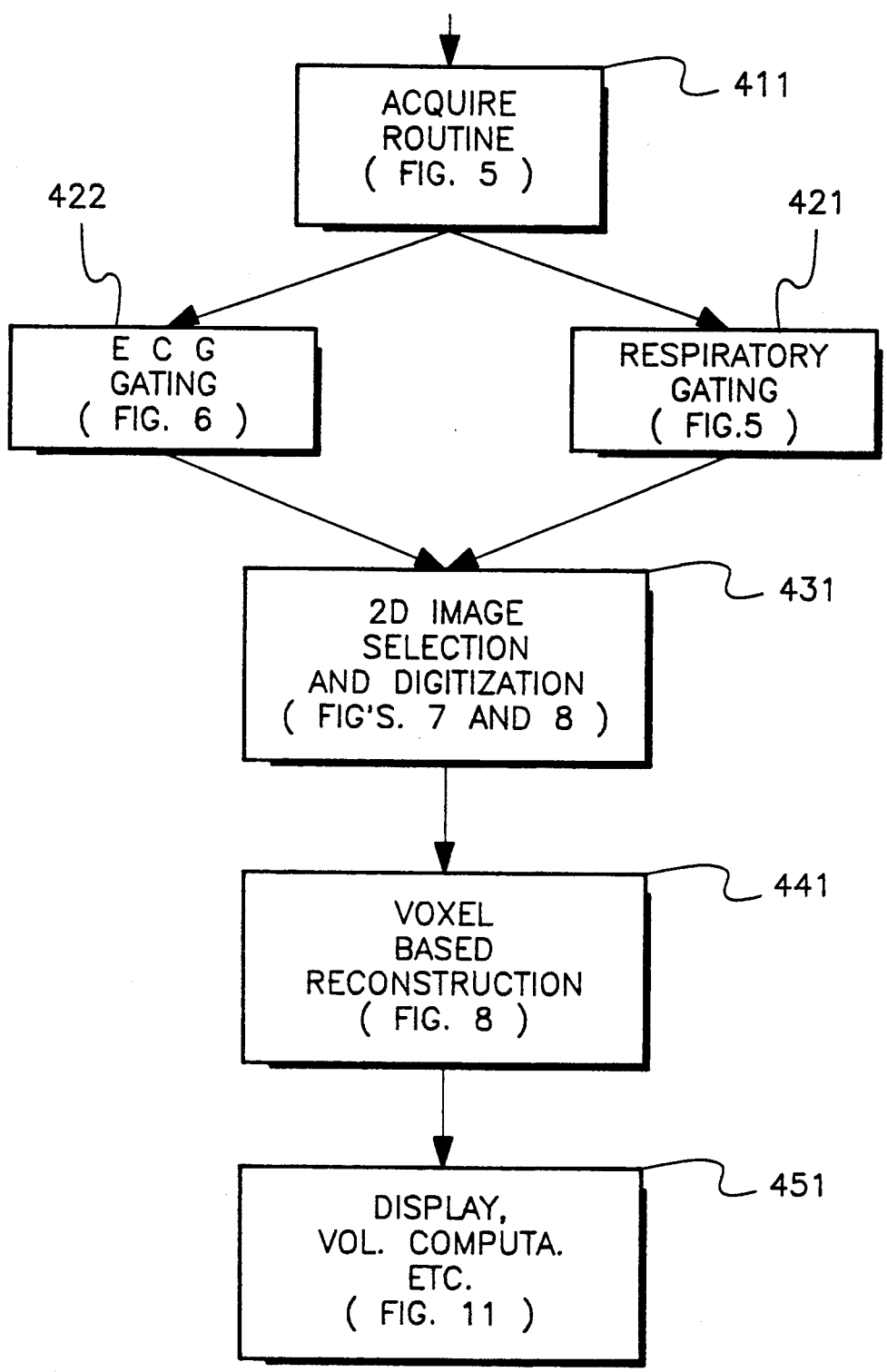
FIG. 4 is a flow diagram which summarizes the procedures of an embodiment of the invention which are implemented in accordance with the flow diagrams of subsequent FIGS. 4–11.
Figure 6:
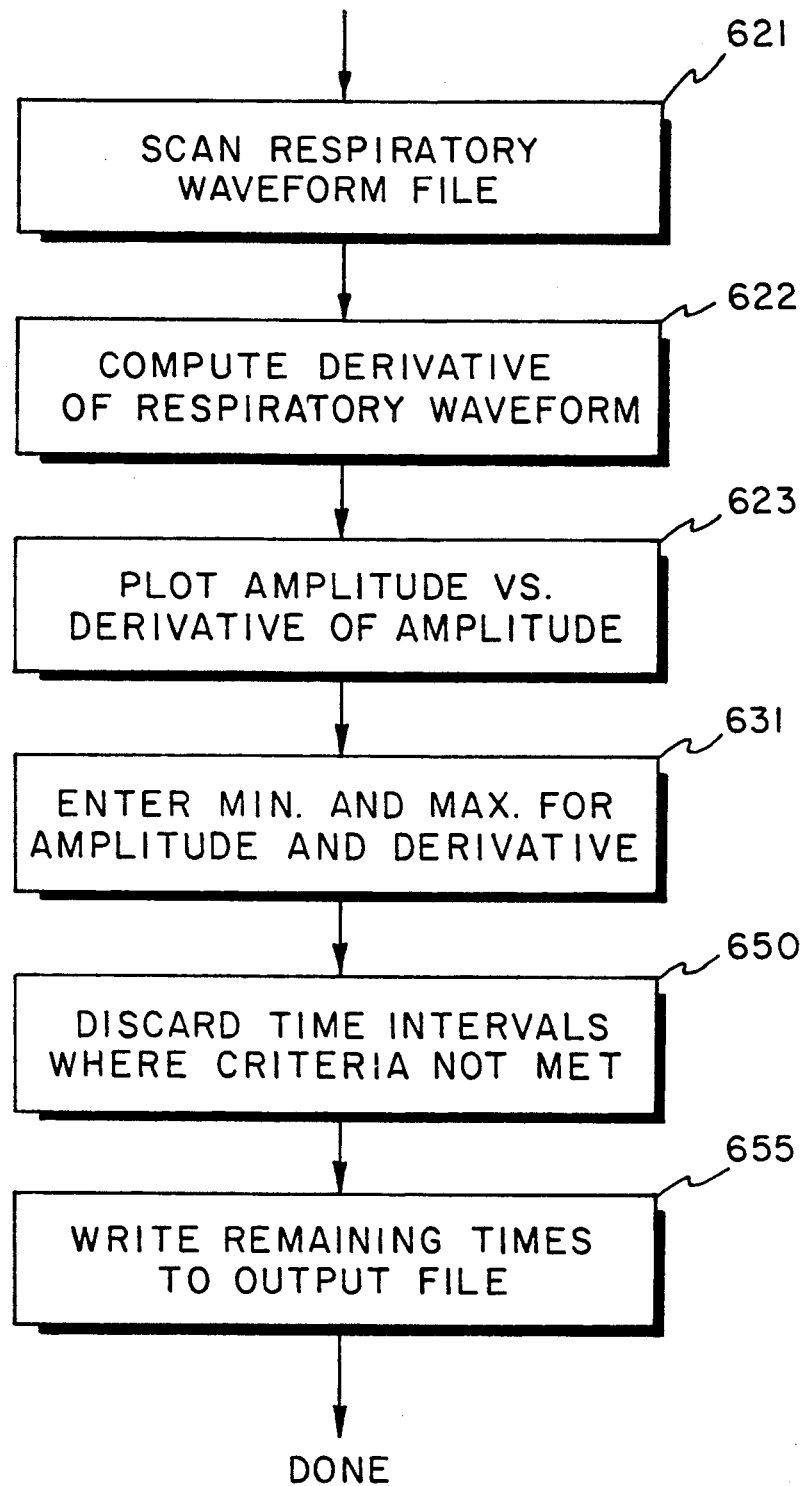
FIG. 6 is a flow diagram of a routine for programming the processor for obtaining gating signals from the respiratory information.
Figure 7:
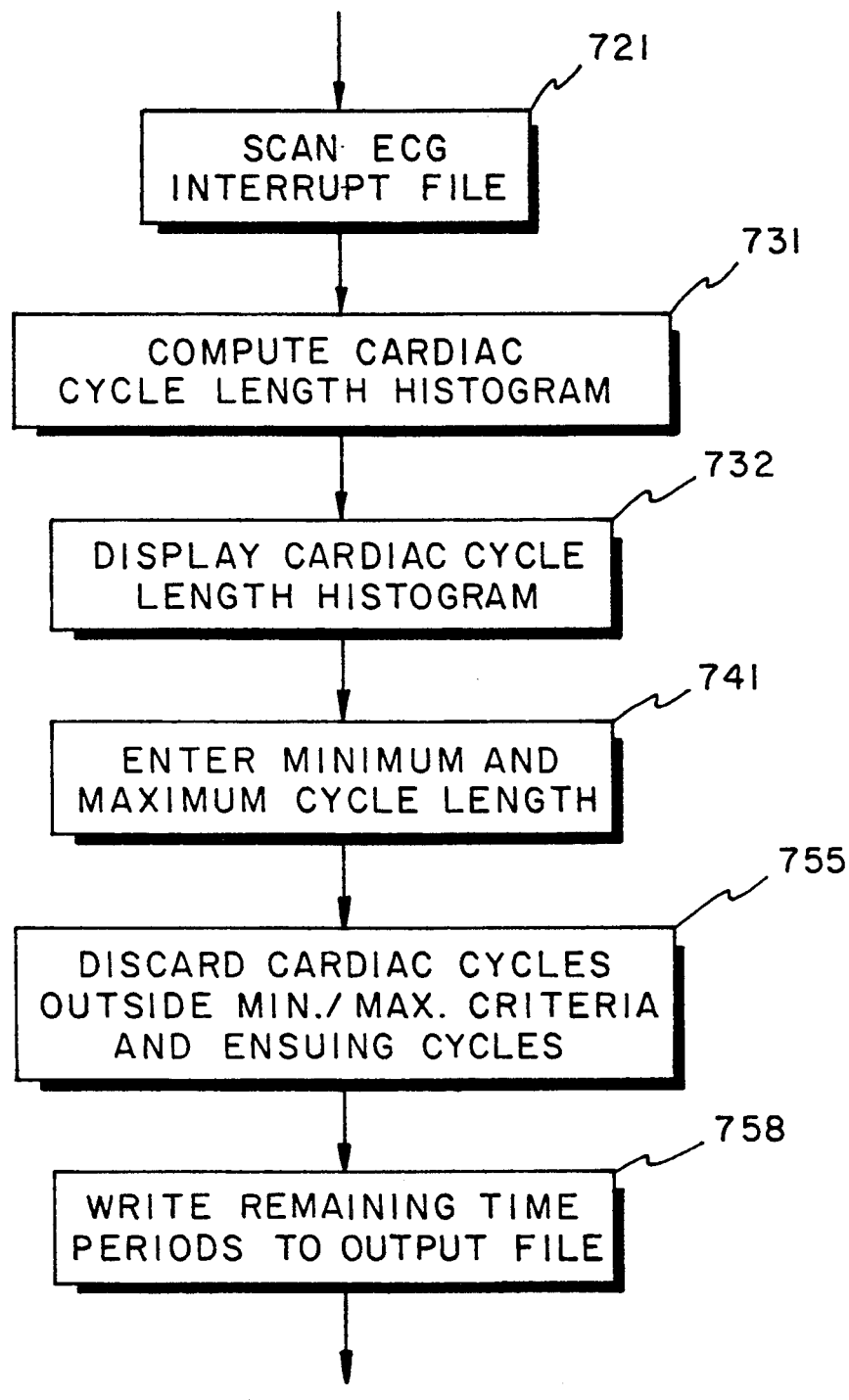
FIG. 7 is a flow diagram of a routine for programming the processor for obtaining gating signals from the electorcardiographic information.
Figure 8A:
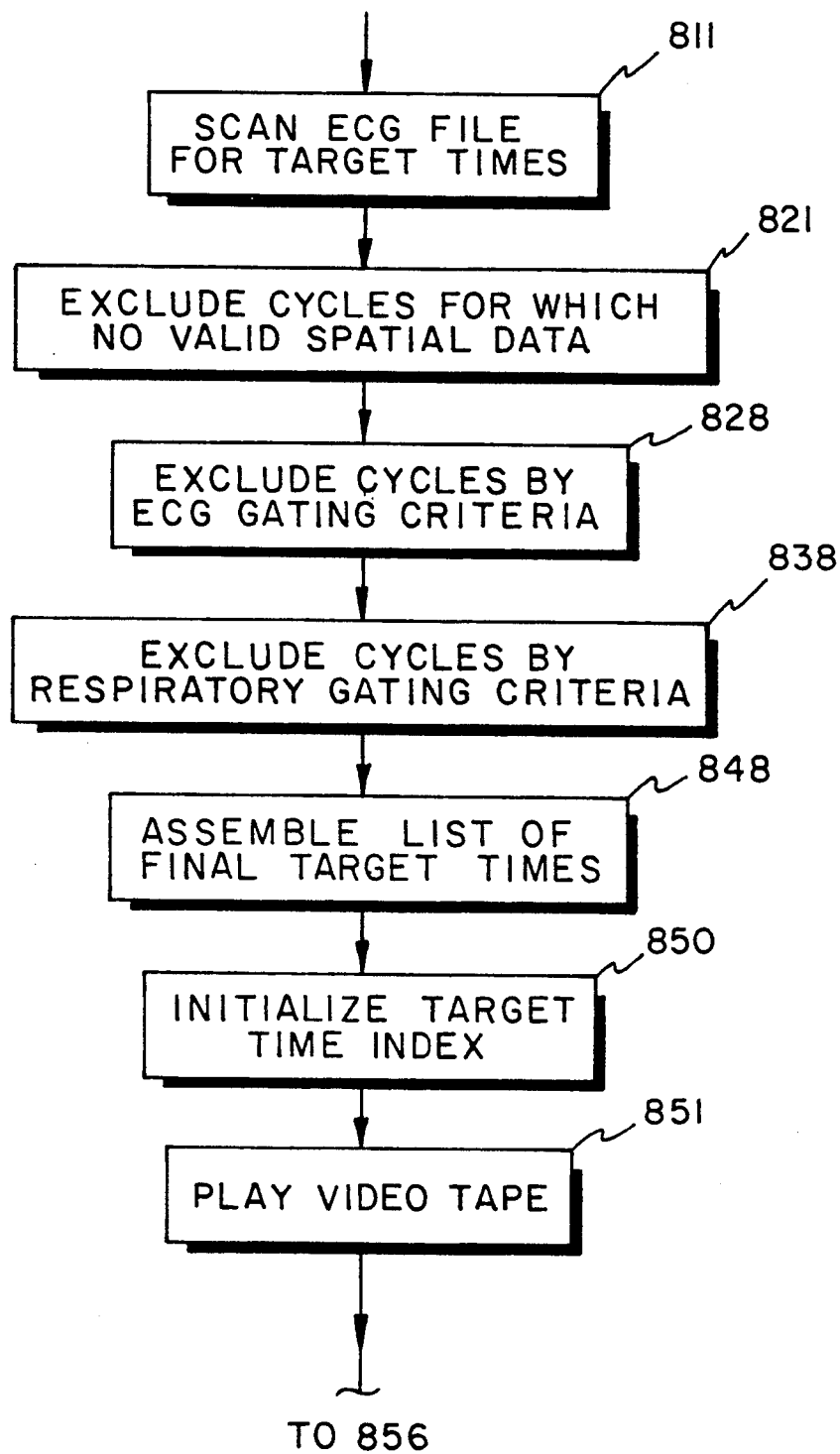
FIGS. 8A and 8B, is a flow diagram for controlling the processor for selection of frames to be digitized and stored.
Figure 8B:
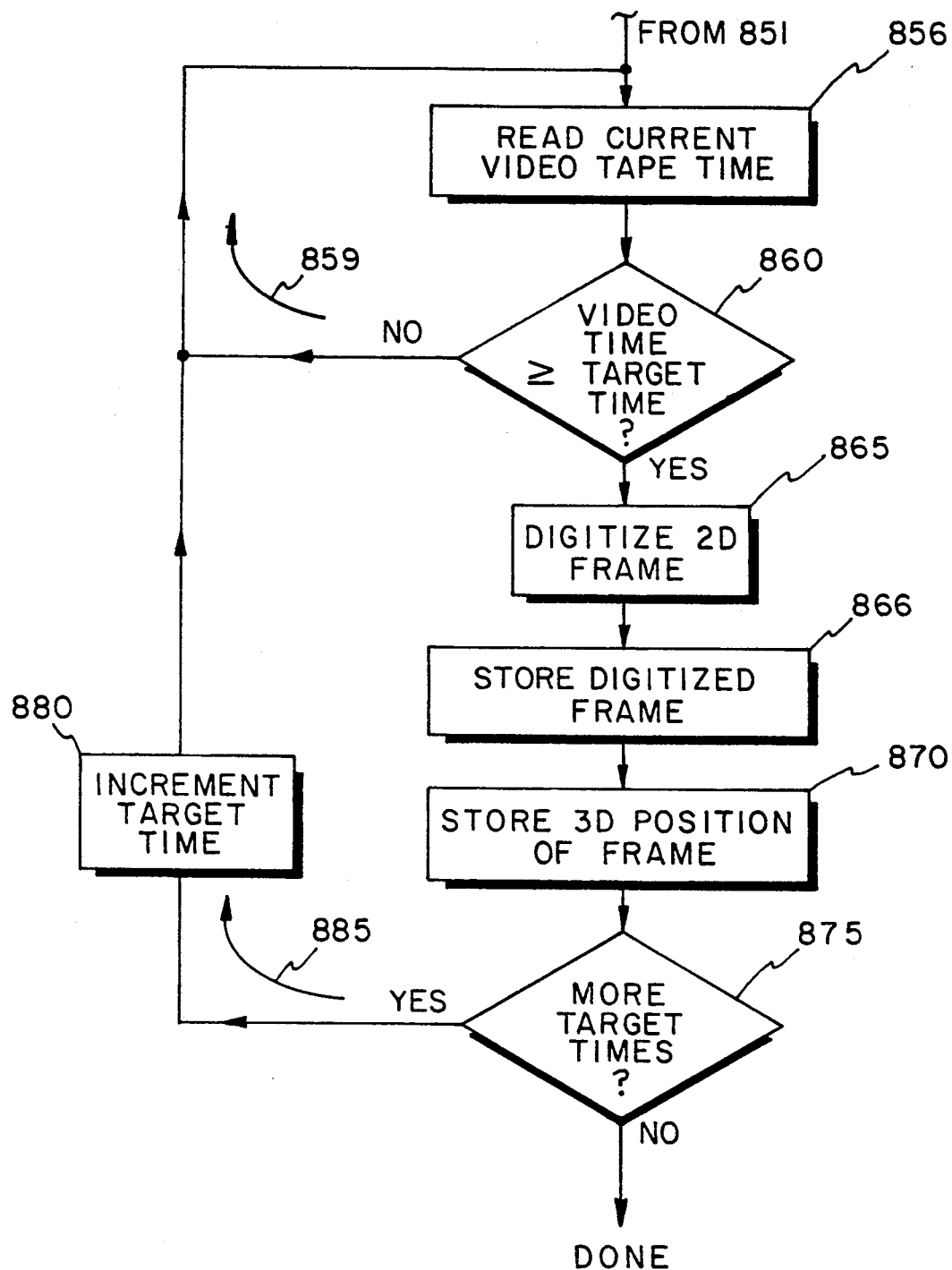

Referring to FIG. 4, there is shown a flow diagram which summarizes the procedures of the present embodiment which are individually implemented in accordance with the flow diagrams of subsequent FIGS. 4-11. The block 411 represents the routine called Acquire, which is described in conjunction with FIG. 5. During the Acquire routine, frames of data obtained with the 2D ultrasonic imaging equipment are stored in conjunction with a time reference and with data from the 3D digitizer that is used to derive the position and orientation of the transducer 21. Also, inputs from the ECG monitor 131 and respiratory monitor 132 are stored in conjunction with timing information. In the present embodiment, the ECG cycle information and respiratory information are used retrospectively to gate the image data; i.e., only frames taken during portions of these cycles that are favorable for consistent imaging are selected for further processing. The routines for developing the gating signals, described in conjunction with FIGS. 5 and 6, are represented in FIG. 4 by the blocks 421 and 422, respectively. The block 431, as described in conjunction with the routines of FIGS. 7 and 8, represents the selection of frames for further processing in accordance with the previously developed gating information, and the digitization of these frames. Next, the block 441 represents the routine of described in conjunction with FIG. 8 for reconstructing a three-dimensional model of the body region being imaged by mapping the individual two-dimensional image frames into a 3D voxel space. The block 451 represents the routine of FIG. 9 for displaying of image information from the 3D voxel space, as well as options such as rendering and volume calculation based on image data in the voxel space.

Referring to FIG. 5, there is shown a flow diagram of the routine for acquiring the image data and positional data. The first block 511 represents initialization of the equipment, including any necessary calibration of the 3D digitizer and the 2D ultrasonic imaging equipment. The block 112 is then entered, this block representing the entering of data concerning the patient to be examined; i.e., the patient's name, weight, and other desired information for record keeping purposes. The block 513 is then entered, this block representing the digitizing and storage of the three operator-designated points (a, b, and e) on the patient's chest which, as described above, are subsequently used to transform image points from digitizer coordinates to a conventional system of anatomic axes. This set of anatomic axes is defined by the unit vectors i, j, k, as first described above in conjunction with FIG. 3. The operator can be prompted to input the three points by any suitable means, for example, by touching the transducer head in sequence to the three points, and at each point, inputting a command to compute the transducer position. The coordinates produced by the digitizer for each of the three points (a, b, and e) are used to calculate and store the unit vectors $\hat{i}$, $\hat{j}$, $\hat{k}$, in accordance with equations (9), (10) and (11), as represented by the blocks 515 and 516. The block 521 is then entered, this block representing the initialization of a 10 ms. timer, which is used in the present embodiment to time correlate the imaging data, the positional data, and the gating information. Next, the video tape record is started, and the obtainment of video images with the 2D ultrasonic imaging system is initiated (block 525). The block 530 is then entered, this block representing the scanning of the keyboard for mode change. Inquiry is made (diamond 540) as to whether a function key has been hit. If so, as indicated in the diagram, the individual function key that has been hit determines which of the blocks 541-545 is entered. The block 541 (function key F1) represents restarting of the acquisition process. The block 542 (function key F2) represents the suspending of acquisition. The block 543 (function key F4) represents the control over the real-time display mode, the function key F4 serving as a toggle to turn this mode on and off. The block 544 (function key F5) represents the clearing of the real time reconstruction space. The block 545 (function key F10) represents termination of the acquisition procedure, whereupon the timing counter is stopped, and equipment functions are terminated.

If the inquiry of diamond 540 was answered in the negative, the blocks 551 and 552 are successively entered, these blocks respectively representing the storing of any intercurrent ECG interrupt times, and the digitizing and storage of the current respiratory waveform value from the respiratory monitor. The block 561 is then entered, this block representing the storing of the 3D digitizer inputs. These inputs are then used (block 562) to calculate and store the transducer position (P) and orientation ($\hat{l}$, $\hat{m}$, $\hat{n}$) in accordance with equations (5), (6), (7), and (8). Inquiry is then made (diamond 570) as to whether the real-time display mode is active. If not, block 530 is reentered. If the real-time display mode is active, the current 2D frame is digitized (block 580), the frame's pixel array is projected into the contents of the second voxel space storage is displayed (block 590). The block 530 is then re-entered.

Referring to FIG. 6, there is shown a flow diagram of the routine for selecting the portions of the respiratory cycles during which acquired imaging data is to be deemed acceptable. The block 621 represent the scanning of the respiratory waveform file. The blocks 622 and 623 are then entered, these blocks representing the computation of the derivative of the respiratory signal amplitude with respect to time, and the display of respiratory amplitude verses the derivative of same. In the present embodiment, the portion of the respiratory cycle to be utilized is defined within operator-selected limits. The block 630 represents the selection of minimum and maximum values for the respiratory amplitude and the derivative of respiratory amplitude. The block 650 is then entered, this block representing the discarding of time intervals where the respiratory signal or its derivative fall outside the operator-selected limits. The remaining time intervals are then written to an output file, as represented by the block 655.

Referring to FIG. 7, there is shown a flow diagram of the routine for generating the electrocardiogram (ECG) gating signal. The block 721 is initially entered, this block representing the scanning of the ECG interrupt time file. A histogram of cardiac cycles lengths is computed and displayed (blocks 731 and 732). After viewing the histogram, the operator can select a range of acceptable cardiac cycle lengths, so as to eliminate unusually short or unusually long cycles which are considered non-representative of normal cardiac rhythm. The entering of the operator-selected minimum and maximum cycle lengths is represented by the block 741. The block 755 is then entered, this block representing the discarding of the time periods corresponding to cardiac cycles outside the operator-selected limits and, in each case, the ensuing cycle. The remaining time periods are then written to the output gating file, as represented by the block 758.

Referring to FIG. 8, there is shown a routine for selecting the 2D image frames to be digitized (based, inter alia, on the gating information), and for digitizing the selected frames. The block 811 represents the selection of target times for which frames are to be selected, and in the present embodiment the ECG interrupts are used to select diastolic frames. However, any desired time or times during the cardiac cycle can be selected for imaging. The block 821 is then entered, this block representing the exclusion of time periods for which there is no valid 2D imaging data. The ECG and respiratory gating files are then used (blocks 828 and 838, respectively) to exclude cycles in accordance with these gating criteria. A list of final target times which have valid spatial data and have met all gating criteria, is then assembled (block 848). A target time index is intialized at the first target time (block 850). Next, the playing of the video tape is initiated, as represented by the block 851. The current video tape time is read (block 856, and is compared with the current target time (diamond 860). If the current video tape time is less than the current target time, the block 856 is re-entered, and the loop 859 continues until the current video time is equal to or greater than the current target time. When this occurs, the frame on the video tape corresponding to the current video tape time is digitized and stored, as represented by the blocks 865 and 866, respectively. The 3D position that had been recorded on the video tape in conjunction with the 2D video frame is also stored (block 870), again in association with the related 2D frame. Inquiry is then made (diamond 875) as to whether there are more target times. If so, the target time is incremented to the next target time on the list (block 880), and the block 856 is re-entered. The loop 885 then continues until all target times on the list have been considered.

Figure 9:
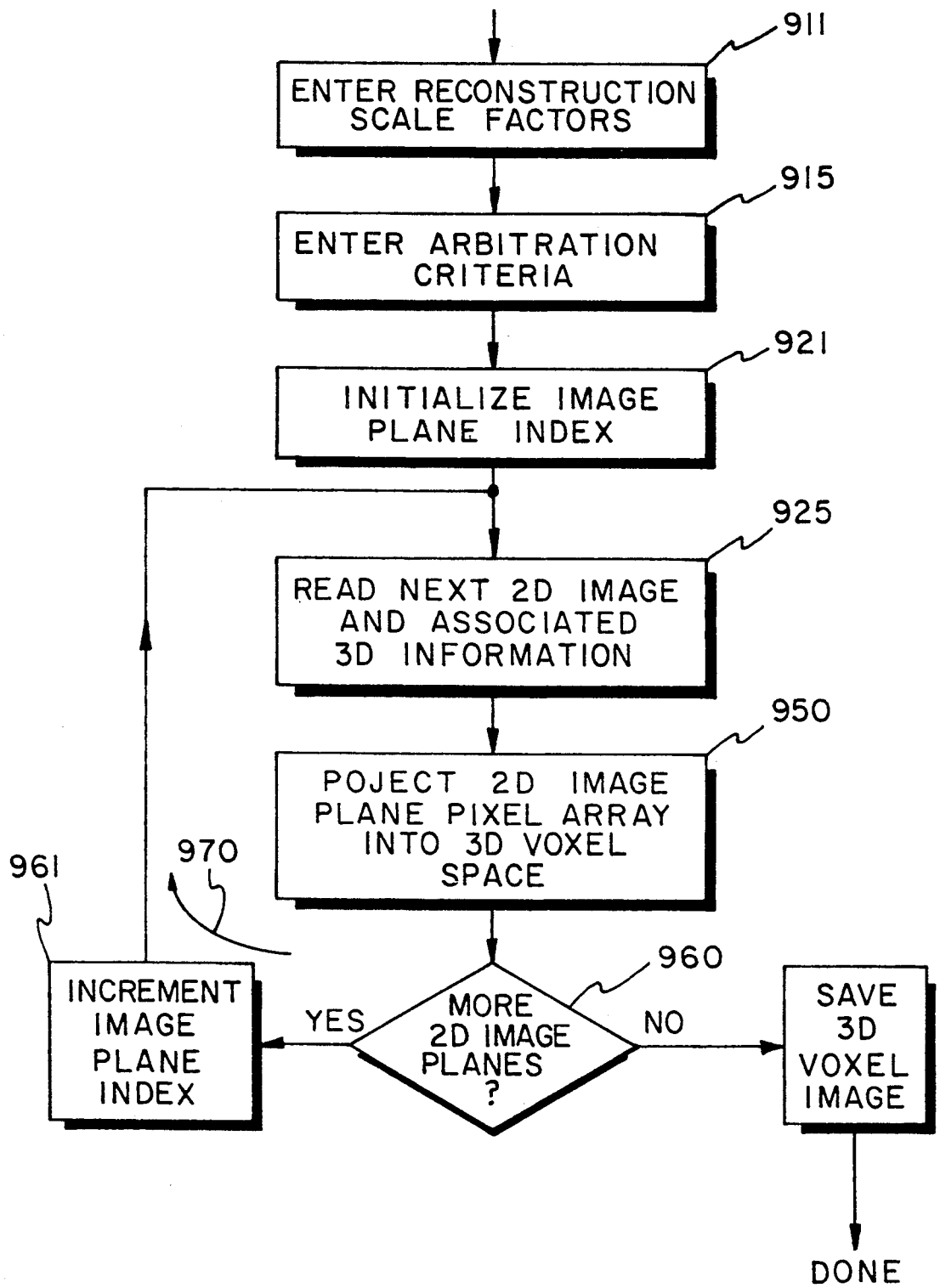
FIG. 9 is a routine for controlling the processor for utilizing the stored 2D images to obtain a 3D image reconstruction.

Referring to FIG. 9, there is shown a flow diagram of the routine for utilizing the stored 2D images to obtain a 3D image reconstruction; i.e., a 3D voxel space containing voxels with values that are based on the mapping of the pixel values of the 2D images into the 3D voxel space. The block 911 is entered, this block representing the entering of the reconstruction scale factors $s_v$, $s_h$, and $s_{vox}$. The block 915 is then entered, this block representing the entering of arbitration criteria. The arbitration criteria are the rules for determining the value to be entered at a particular voxel space when that voxel space already contains a previously entered value. For example, the new voxel value can be obtained as an average of the existing voxel value and the pixel value that is being mapped into that voxel. Various other rules for obtaining voxel values can be utilized. The block 921 is then entered, this block representing the initalizing of an index for the 2D image planes and associated 3D position and orientation information. The next 2D image and associated 3D position and orientation information is then read (block 925), and the 2D video plane is then projected into the 3D voxel space (block 950) in accordance with the relationships set forth above. The routine represented by the block 950 is described in conjunction with FIG. 10. Inquiry is then made (diamond 960) as to whether there are more 2D image planes to project into the voxel space. If so, the 2D image plane index is incremented (block 961), and the block 925 is reentered. The loop 970 is then continued until all 2D image planes have been processed, whereupon the voxel image in the 3D frame buffer can be transferred to bulk storage (block 985).

Figure 10A:
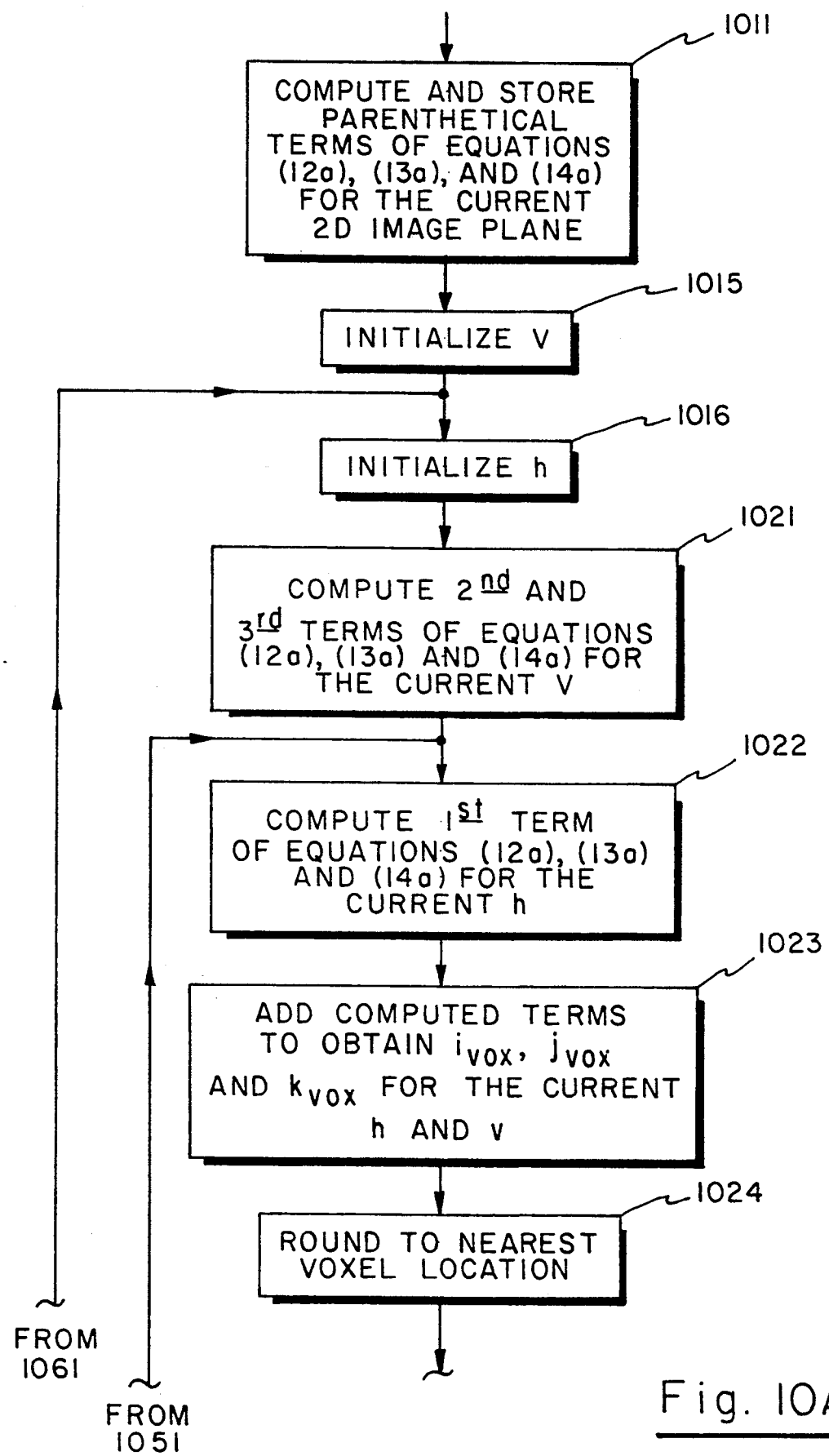
FIGS. 10A and 10B, is a flow diagram of a routine for programming the processor for projecting an individual 2D image plane into the 3D voxel space storage.
Figure 10B:
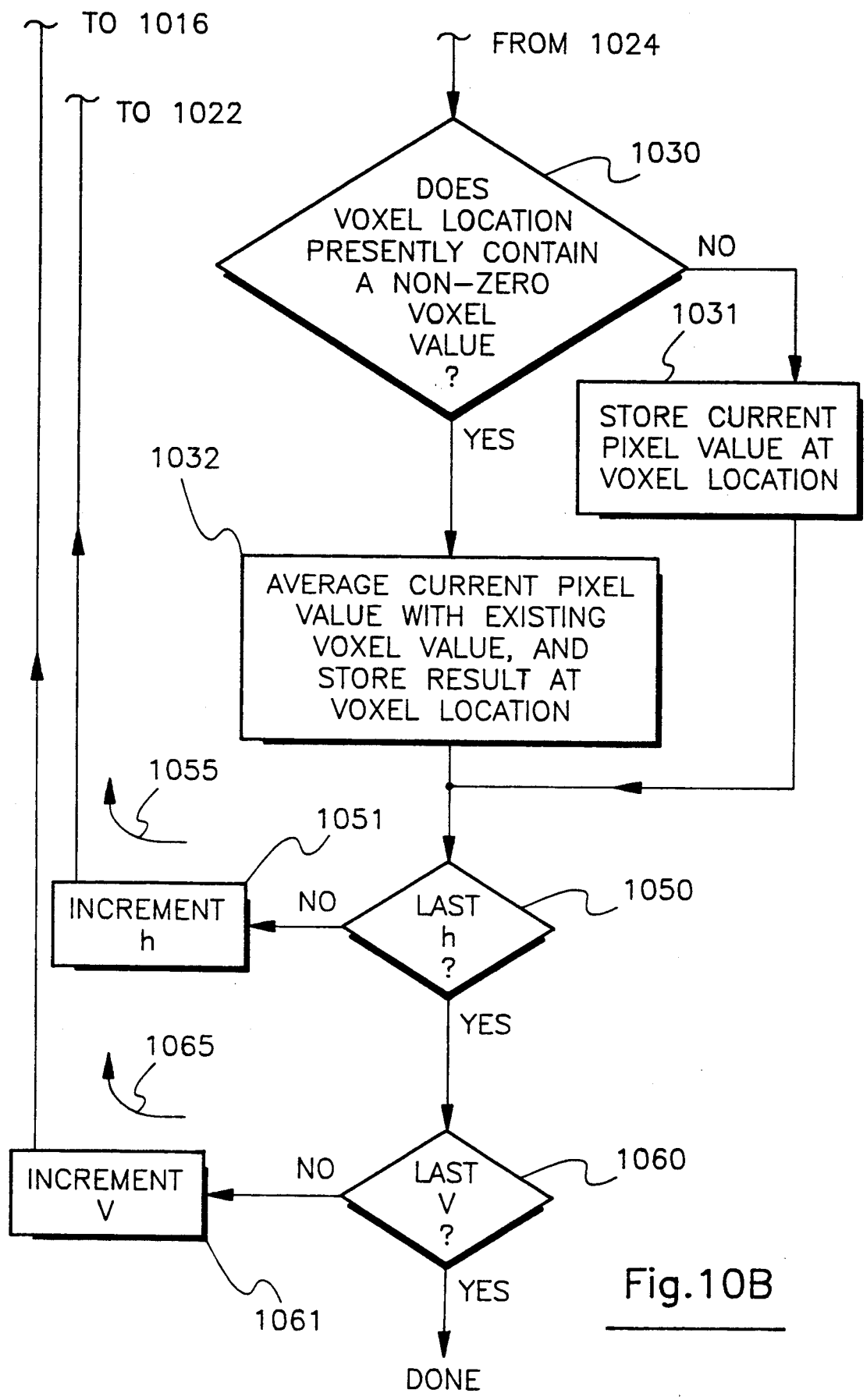

Referring to FIG. 10, there is shown a flow diagram of the routine represented by the block 950 for projecting an individual 2D image plane into the 3D voxel space storage. The block 1011 represents the computing and storing of the parenthetical terms of equations (12a), (13a), and (14a) for the current 2D image plane. The values for $\hat{i}$, $\hat{j}$ and $\hat{k}$ were computed in accordance with the equations (9), (10) and (11) above and were previously stored (FIG. 5). The values of $\hat{l}$, $\hat{m}$, $\hat{n}$ and P were computed in accordance with equations (5), (6), (7) and (8) above for the positional data stored in conjunction with the current 2D image plane, and were previously stored (FIG. 8). The vertical and horizontal position indices for the pixel of the current 2D image plane are initialized, as represented by the blocks 1015 and 1016, respectively. The block 1021 is then entered, this block representing the computation of the second and third terms of equations (12a), (13a), and (14a) for the current v. This only needs to be computed once for the current v. The block 1022 is next entered, this block representing the computing of the first term of equations (12a), (13a), and (14a) for the current h. The computed terms are then added (block 1023) to obtain $i_{vox}$, $j_{vox}$, and $k_{vox}$ for the current h and v, in accordance with the equations (12a), (13a), and (14a). The obtained coordinate values are then rounded to the nearest voxel location, as represented by the block 1024. Inquiry is then made (diamond 1030) as to whether the current voxel location ($i_{vox}$, $j_{vox}$, $k_{vox}$) presently contains a non-zero voxel value, where zero represents an empty voxel. If not, the current pixel value (i.e., the pixel value at pixel location (h,v) of the current 2D image plane) is stored at the current voxel location (block 1031). If, however, the current voxel location contains a non-zero voxel value, than the current pixel value is averaged with the existing voxel value, and the result is stored at the current voxel location (block 1032). This means that the present embodiment is employing the arbitration criterion referred to above, although it will be understood that other criterion can be employed. The diamond 1050 is then entered, and inquiry is made as to whether the last h has been reached. If not, h is incremented (block 1051), the block 1022 is re-entered, and the loop 1055 is continued until all h values for the current v of the pixel array of the current 2D image plane have been processed. When this is complete, inquiry is made (diamond 1060) as to whether the last v has been reached. If not, v is incremented (block 1061), and the loop 1065 is continued until all values of v of the pixel array have been processed. [If the real time display mode is active, the incrementing of h and v can reflect the reduction in pixels being projected.]

Figure 11:
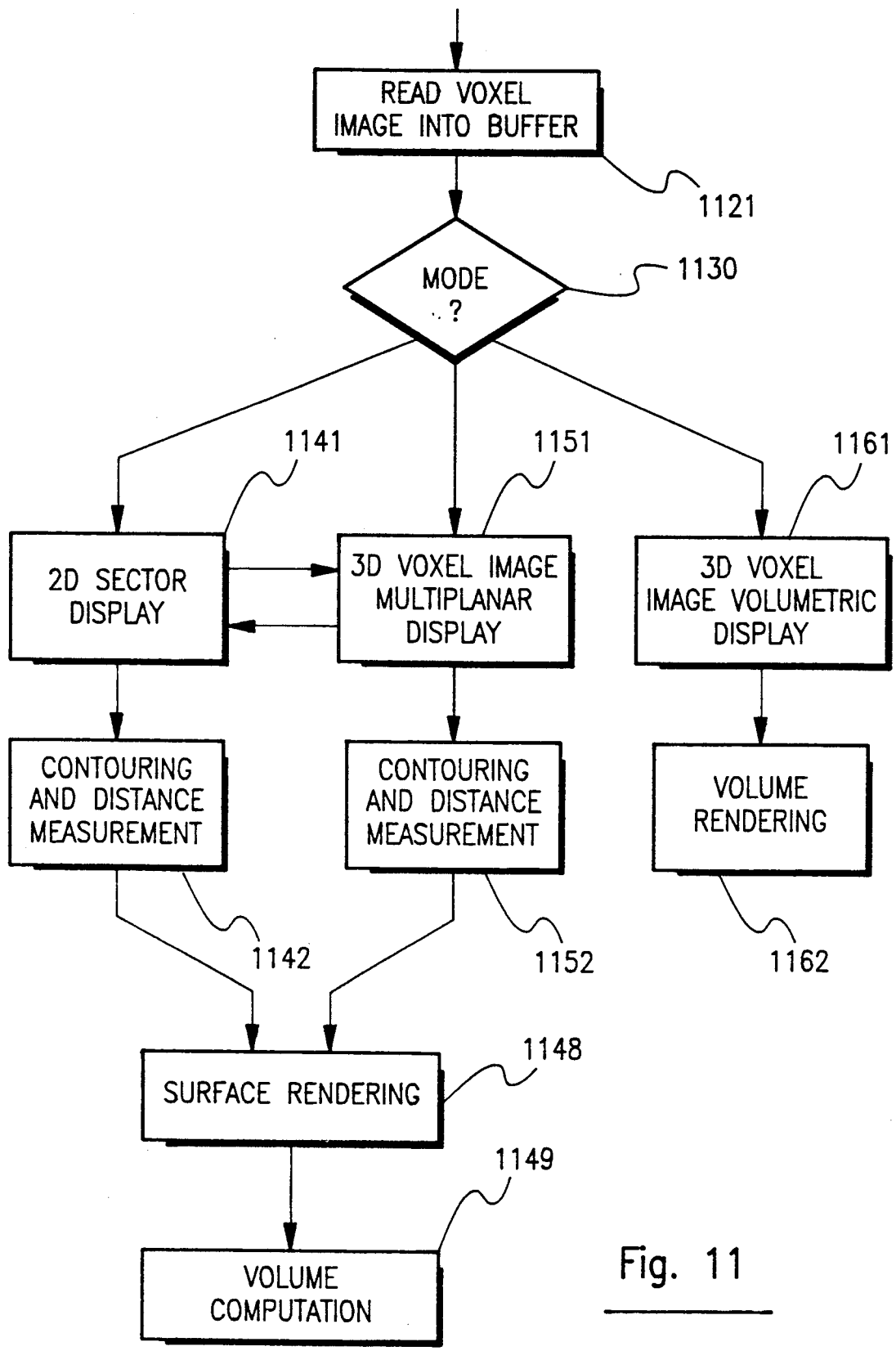
FIG. 11 is a flow diagram of a routine for programming the processor for displaying of image information.

Referring to FIG. 11, there is shown a flow diagram of the routine for displaying image information. It will be understood that numerous techniques are known in the art for displaying images contained in a 2D frame buffer or a 3D frame buffer, and the present invention is not, per se, based on novel features of a particular display technique. In this regard, it will be understood that any of the image information previously described and stored in any of the storage media hereof, or available from the 2D image scanner, in real-time or otherwise, can be displayed in any appropriate fashion. Accordingly, the illustrative flow diagram of FIG. 11 shows examples of the types of displays that can be generated from the image representations produced in accordance with the present embodiment of the invention. The block 1121 represents the reading of a voxel image into the 3D image buffer 117 (FIG. 1). The image buffer may already contain an image to be displayed or, as indicated by the block 1121, the voxel image can be transferred from another storage medium, such as magnetic tape or other suitable bulk storage medium. A display mode is then selected (diamond 1130). In this example, one of the available modes is a 2D sector display, whereby any desired section through the voxel space can be selected and displayed (block 1141). Contouring and distance measurement (block 1142) can also be performed on the 2D image. Routines for implementing these functions are known in the art, and programs therefor are commercially available. The same is true of surface rendering and volume computation functions, which are represented by the blocks 1148 and 1149, respectively. Another selected mode provides a multiplanar display of the 3D voxel image (block 1151). This block 1151 is shown as communicating with block 1141 which involves display of a single 2D sector. Again, a contouring and distance measurement function is represented (block 1152), and surface rendering and volume computation can be implemented. In a further display mode, a 3D voxel image volumetric display is provided (block 1161), and volume rendering can also be employed (block 1162).

The invention has been described with reference to a particular preferred embodiment, but variations within the spirit and scope of the invention will occur to those skilled in the art. For example, if desired, multiple phases of the cardiac cycle can be imaged, either at full resolution or, if desired, at reduced resolution in real time if sufficient computing power is not available.

What is claimed is:

1. Apparatus for producing a three-dimensional image representation of a body, comprising:

an ultrasonic imaging subsystem for producing signals representative of two-dimensional images of sections of the body, said subsystem including a scanning transducer that is moveable in three dimensions, without constraint of position or orientation within a three-dimensional space, to select the section of the body to be imaged;

means for storing said image representative signals as arrays of digital pixel values, said digital pixel values representing one of a multiplicity of gray scale values;

means, including a three-dimensional digitizer subsystem, for deriving information representative of the three-dimensional position and orientation of the transducer during the scanning of an associated section of the body;

means for storing said information;

means for projecting the arrays of digital pixel values into a three dimensional voxel space, the voxel locations which correspond to projected pixel locations of a given pixel array being determined as a function of the stored position and orientation information associated with the section of the body from which the given pixel array was obtained, said projection means including means for determining if an existing non-zero gray scale value is already present at a given voxel location to which a current pixel value with said existing voxel value and storing the resulting average value as a new voxel value at said given voxel location; and voxel space storage means for storing the voxel values projected into the voxel space.

2. Apparatus as defined by claim 1, wherein said means for projecting the arrays of digital pixel values into said voxel space includes means for determining said voxel locations for a particular pixel array by computing a given voxel location as a function of the two-dimensional coordinates of a given pixel being projected and of said position and orientation information, and then by computing subsequent voxel locations for subsequently projected pixels by taking values obtained during computation of the projected location of a neighboring pixel and adding a value which depends on the incrementing of the pixel coordinates with respect to the neighboring pixel.

3. Apparatus as defined by claim 2, further comprising a second voxel space storage means for storing a three dimensional array of voxel values, said second voxel space storage means having a small fraction of the number of voxels of said first-mentioned voxel space storage means, and wherein said projecting means includes means for projecting lower resolution versions of said pixel arrays into a second three dimensional voxel space and for storing the voxel values projected into said second voxel space in said second voxel space storage means in real-time with respect to the obtainment of said signals representative of two-dimensional images of sections of the body.

4. Apparatus as defined by claim 2, further comprising means for displaying images based on the contents of said voxel space storage means.

5. Apparatus as defined by claim 1, wherein said three dimensional digitizer subsystem is an acoustic digitizer subsystem, and wherein said subsystem includes three sound emitters mounted in conjunction with said transducer, one of said second emitters being mounted behind said transducer and on the central line of the scan field of said transducer, and the other two of said second emitters being mounted behind said one sound emitter and on opposite sides of said central line and equidistant therefrom.

6. Apparatus as defined by claim 5, wherein said subsystem further includes a plurality of sound receivers spaced from said sound emitters, and means responsive to the outputs of said sound emitters for obtaining the coordinate locations of said sound emitters, and wherein said means for deriving information includes means responsive to said coordinate locations for generating vector representation quantities which define the position and orientation of said transducer.

7. Apparatus as defined by claim 6, wherein said sound emitters are mounted on a cross-bar that is rigidly secured to said transducer.

8. Apparatus as defined by claim 5, wherein said means for projecting the arrays of digital pixel values into said voxel space storage means includes means for determining said voxel locations for a particular pixel array by computing a given voxel location as a function of the two-dimensional coordinates of a given pixel being projected and of said position and orientation information, and then by computing subsequent voxel locations for subsequently projected pixels by taking values obtained during computation of the projected location of a neighboring pixel and adding a value which depends on the incrementing of the pixel coordinates with respect to the neighboring pixel.

9. Apparatus as defined by claim 1, further comprising a second voxel space storage means for storing a three dimensional array of voxel fraction of the number of voxels of said first-mentioned voxel space storage means, and wherein said projecting means includes means for projecting lower resolution versions of said pixel arrays into a second three dimensional voxel space and for storing the voxel values projected into said second voxel space in said second voxel space storage means in real-time with respect to the obtainment of said signals representative of two-dimensional images of sections of the body.

10. Apparatus as defined by claim 9, further comprising means for displaying images based on the contents of said second voxel space storage means.

11. Apparatus as defined by claim 10, further comprising means for also displaying images based on the contents of said first-mentioned voxel space storage means.

12. Apparatus as defined by claim 1, further comprising means for displaying images based on the contents of said voxel space storage means.

13. Apparatus as defined by claim 1, wherein said body is a human body, and further comprising means for generating signals which depend upon the respiratory and cardiac patterns of the body; means for generating selection control signals as a function of the signals which depend on the respiratory and cardiac patterns; and means for selecting the arrays of pixels to be projected as a function of said selection control signals.

14. Apparatus as defined by claim 13, wherein said selection control signals are used to determine which of the image representative signals are stored as arrays of digital pixel values.

15. A method for producing a three-dimensional image representation of a body, comprising the steps of:
producing signals representative of two-dimensional images of sections of the body with an ultrasonic imaging subsystem which includes a scanning transducer that is moveable in three dimensions, without constraint of position or orientation within a three-dimensional space, to select the section of the body to be imaged;
storing said image representative signals as arrays of digital pixel values, said digital pixel values representing one of a multiplicity of gray scale values;
deriving, with a three-dimensional digitizer subsystem, information representative of the three dimensional position and orientation of the transducer during the scanning of an associated section of the body;
storing said information;
projecting the arrays of digital pixel values into a three-dimensional voxel space, the voxel locations which correspond to projected pixel locations of a given pixel array being determined as a function of the stored position and orientation information associated with the section of the body from which the given pixel array was obtained, determining if an existing non-zero gray scale value is already present at a given voxel location to which a current pixel value is projected and, if so, averaging said current pixel value with said existing voxel value and storing the resulting average value as a new voxel value at said given voxel location; and
storing the voxel values projected into the voxel space.

16. The method as defined by claim 15, wherein said step of projecting the arrays of digital pixel values into said voxel space storage includes determining said voxel locations for a particular pixel array by computing a given voxel location as a function of the two-dimensional coordinates of a given pixel being projected and of said position and orientation information, and then computing subsequent voxel locations for subsequently projected pixels by taking values obtained during computation of the projected location of a neighboring pixel and adding a value which depends on the incrementing of the pixel coordinates with respect to the neighboring pixel.

* * * * *